US008758801B2

(12) United States Patent
Pacetti et al.

(10) Patent No.: US 8,758,801 B2
(45) Date of Patent: Jun. 24, 2014

(54) COATINGS FOR IMPLANTABLE DEVICES COMPRISING POLY(HYDROXY-ALKANOATES) AND DIACID LINKAGES

(71) Applicant: Advanced Cardiovascular Systems, Inc., Santa Clara, CA (US)

(72) Inventors: Stephen Dirk Pacetti, San Jose, CA (US); Thierry Glauser, Redwood City, CA (US)

(73) Assignee: Abbott Cardiocascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/686,392

(22) Filed: Nov. 27, 2012

(65) Prior Publication Data

US 2013/0116380 A1    May 9, 2013

Related U.S. Application Data

(62) Division of application No. 10/902,982, filed on Jul. 30, 2004, now Pat. No. 8,357,391.

(51) Int. Cl.
*A61F 2/00* (2006.01)
*C08G 63/00* (2006.01)
*C08G 63/08* (2006.01)
*C08G 63/91* (2006.01)
*C08G 67/00* (2006.01)
*C08G 69/00* (2006.01)
*C08L 67/00* (2006.01)

(52) U.S. Cl.
USPC ............ 424/426; 525/415; 528/271; 528/354

(58) Field of Classification Search
None
See application file for complete search history.

(56) References Cited

U.S. PATENT DOCUMENTS

| | | | |
|---|---|---|---|
| 2,072,303 A | 3/1937 | Herrmann et al. | 128/335.5 |
| 2,386,454 A | 10/1945 | Frosch et al. | 260/78 |
| 3,773,737 A | 11/1973 | Goodman et al. | 260/78 |
| 3,849,514 A | 11/1974 | Gray, Jr. et al. | 260/857 |
| 4,226,243 A | 10/1980 | Shalaby et al. | 128/335.5 |
| 4,329,383 A | 5/1982 | Joh | 428/36 |
| 4,343,931 A | 8/1982 | Barrows | 528/291 |
| 4,529,792 A | 7/1985 | Barrows | 528/291 |
| 4,611,051 A | 9/1986 | Hayes et al. | 528/295.3 |
| 4,656,242 A | 4/1987 | Swan et al. | 528/295.3 |
| 4,733,665 A | 3/1988 | Palmaz | 128/343 |
| 4,800,882 A | 1/1989 | Gianturco | 128/343 |
| 4,882,168 A | 11/1989 | Casey et al. | 424/468 |
| 4,886,062 A | 12/1989 | Wiktor | 128/343 |
| 4,931,287 A | 6/1990 | Bae et al. | 424/484 |
| 4,941,870 A | 7/1990 | Okada et al. | 600/36 |
| 4,977,901 A | 12/1990 | Ofstead | 128/772 |
| 5,019,096 A | 5/1991 | Fox, Jr. et al. | 623/1 |
| 5,100,992 A | 3/1992 | Cohn et al. | 424/501 |
| 5,112,457 A | 5/1992 | Marchant | 204/165 |
| 5,133,742 A | 7/1992 | Pinchuk | 623/1 |
| 5,163,952 A | 11/1992 | Froix | 623/1 |
| 5,165,919 A | 11/1992 | Sasaki et al. | 424/488 |
| 5,202,413 A | 4/1993 | Spinu | 528/354 |
| 5,219,980 A | 6/1993 | Swidler | 528/272 |
| 5,258,020 A | 11/1993 | Froix | 623/1 |
| 5,272,012 A | 12/1993 | Opolski | 428/423.1 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,306,786 A | 4/1994 | Moens et al. | 525/437 |
| 5,324,775 A | 6/1994 | Rhee et al. | 525/54.2 |
| 5,328,471 A | 7/1994 | Slepian | 604/101 |
| 5,330,768 A | 7/1994 | Park et al. | 424/501 |
| 5,380,299 A | 1/1995 | Fearnot et al. | 604/265 |
| 5,417,981 A | 5/1995 | Endo et al. | 424/486 |
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A | 11/1995 | Berg et al. | 427/2.3 |
| 5,485,496 A | 1/1996 | Lee et al. | 378/64 |
| 5,514,380 A | 5/1996 | Song et al. | 424/426 |
| 5,516,881 A | 5/1996 | Lee et al. | 528/320 |
| 5,569,463 A | 10/1996 | Helmus et al. | 424/426 |
| 5,578,073 A | 11/1996 | Haimovich et al. | 623/1 |
| 5,578,325 A | 11/1996 | Domb et al. | 424/501 |
| 5,584,877 A | 12/1996 | Miyake et al. | 623/1 |
| 5,605,696 A | 2/1997 | Eury et al. | 424/423 |
| 5,607,467 A | 3/1997 | Froix | 623/1 |
| 5,609,629 A | 3/1997 | Fearnot et al. | 623/1 |

(Continued)

FOREIGN PATENT DOCUMENTS

DE    42 24 401    1/1994
EP    0 301 856    2/1989

(Continued)

OTHER PUBLICATIONS

Bae et al. Journal of Controlled release 2000 64:3-13.*
Huang et al. Macromolecular Chemistry and Physics 2003 204:1994-2001.*
Choi et al. Journal of Controlled Release 1998 54:39-48.*
Anonymous, *Cardiologists Draw—Up the Dream Stent*, Clinica 710:15 (Jun. 17, 1996), printed Aug. 25, 2003 (2 pages).
Anonymous, *Heparin-coated stents cut complications by 30%*, Clinica 732:17 (Nov. 18, 1996), printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).

(Continued)

*Primary Examiner* — Juliet C Switzer
*Assistant Examiner* — Caralynne Helm
(74) *Attorney, Agent, or Firm* — Squire Sanders (US) LLP

(57) ABSTRACT

Coatings for an implantable medical device and a method of fabricating thereof are disclosed, the coatings including block-polymers comprising at least one poly(hydroxyacid) or poly(hydroxy-alkanoate) block, at least one block of a biologically compatible polymer and at least one type of linking moiety.

21 Claims, No Drawings

(56) References Cited

U.S. PATENT DOCUMENTS

| | | | |
|---|---|---|---|
| 5,610,241 A | 3/1997 | Lee et al. | 525/411 |
| 5,616,338 A | 4/1997 | Fox, Jr. et al. | 424/423 |
| 5,624,411 A | 4/1997 | Tuch | 604/265 |
| 5,628,730 A | 5/1997 | Shapland et al. | 604/21 |
| 5,644,020 A | 7/1997 | Timmermann et al. | 528/288 |
| 5,649,977 A | 7/1997 | Campbell | 623/1 |
| 5,658,995 A | 8/1997 | Kohn et al. | 525/432 |
| 5,665,831 A | 9/1997 | Neuenschwander et al. | 525/415 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | 606/198 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,711,958 A | 1/1998 | Cohn et al. | 424/423 |
| 5,716,981 A | 2/1998 | Hunter et al. | 514/449 |
| 5,721,131 A | 2/1998 | Rudolph et al. | 435/240 |
| 5,723,219 A | 3/1998 | Kolluri et al. | 428/411.1 |
| 5,735,897 A | 4/1998 | Buirge | 623/12 |
| 5,746,998 A | 5/1998 | Torchilin et al. | 424/9.4 |
| 5,759,205 A | 6/1998 | Valentini | 623/16 |
| 5,776,184 A | 7/1998 | Tuch | 623/1 |
| 5,783,657 A | 7/1998 | Pavlin et al. | 528/310 |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,840,387 A | 11/1998 | Berlowitz-Tarrant et al. | 428/36.91 |
| 5,849,859 A | 12/1998 | Acemoglu | 528/271 |
| 5,851,508 A | 12/1998 | Greff et al. | 424/9.411 |
| 5,854,376 A | 12/1998 | Higashi | 528/288 |
| 5,858,746 A | 1/1999 | Hubbell et al. | 435/177 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,879,713 A | 3/1999 | Roth et al. | 424/489 |
| 5,902,875 A | 5/1999 | Roby et al. | 528/310 |
| 5,905,168 A | 5/1999 | Dos Santos et al. | 562/590 |
| 5,910,564 A | 6/1999 | Gruning et al. | 528/310 |
| 5,914,387 A | 6/1999 | Roby et al. | 528/310 |
| 5,919,893 A | 7/1999 | Roby et al. | 525/411 |
| 5,925,720 A | 7/1999 | Kataoka et al. | 525/523 |
| 5,932,299 A | 8/1999 | Katoot | 427/508 |
| 5,955,509 A | 9/1999 | Webber et al. | 514/772.7 |
| 5,958,385 A | 9/1999 | Tondeur et al. | 424/61 |
| 5,962,138 A | 10/1999 | Kolluri et al. | 428/411.1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,011,125 A | 1/2000 | Lohmeijer et al. | 525/440 |
| 6,015,541 A | 1/2000 | Greff et al. | 424/1.25 |
| 6,033,582 A | 3/2000 | Lee et al. | 216/37 |
| 6,034,204 A | 3/2000 | Mohr et al. | 528/328 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,054,553 A | 4/2000 | Groth et al. | 528/335 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,491 A | 9/2000 | Kohn et al. | 604/502 |
| 6,120,536 A | 9/2000 | Ding et al. | 623/1.43 |
| 6,120,788 A | 9/2000 | Barrows | 424/426 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,136,333 A | 10/2000 | Cohn et al. | 424/423 |
| 6,143,354 A | 11/2000 | Koulik et al. | 427/2.24 |
| 6,153,252 A | 11/2000 | Hossainy et al. | 427/2.3 |
| 6,159,978 A | 12/2000 | Myers et al. | 514/252.1 |
| 6,165,212 A | 12/2000 | Dereume et al. | 623/1.13 |
| 6,172,167 B1 | 1/2001 | Stapert et al. | 525/420 |
| 6,177,523 B1 | 1/2001 | Reich et al. | 525/459 |
| 6,180,632 B1 | 1/2001 | Myers et al. | 514/252.1 |
| 6,203,551 B1 | 3/2001 | Wu | 606/108 |
| 6,211,249 B1 * | 4/2001 | Cohn et al. | 514/772.1 |
| 6,214,901 B1 | 4/2001 | Chudzik et al. | 523/113 |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,245,760 B1 | 6/2001 | He et al. | 514/234.8 |
| 6,248,129 B1 | 6/2001 | Froix | 623/1.42 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,258,371 B1 | 7/2001 | Koulik et al. | 424/422 |
| 6,262,034 B1 | 7/2001 | Mathiowitz et al. | 514/44 |
| 6,270,788 B1 | 8/2001 | Koulik et al. | 424/423 |
| 6,277,449 B1 | 8/2001 | Kolluri et al. | 427/289 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,176 B1 | 10/2001 | Whitbourne | 623/23.59 |
| 6,331,313 B1 | 12/2001 | Wong et al. | 424/427 |
| 6,335,029 B1 | 1/2002 | Kamath et al. | 424/423 |
| 6,344,035 B1 | 2/2002 | Chudzik et al. | 604/265 |
| 6,346,110 B2 | 2/2002 | Wu | 606/108 |
| 6,350,812 B1 | 2/2002 | Vert et al. | 524/845 |
| 6,358,556 B1 | 3/2002 | Ding et al. | 427/2.24 |
| 6,379,381 B1 | 4/2002 | Hossainy et al. | 623/1.42 |
| 6,387,379 B1 | 5/2002 | Goldberg et al. | 424/400 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,482,834 B2 | 11/2002 | Spada et al. | 514/311 |
| 6,494,862 B1 | 12/2002 | Ray et al. | 604/96.01 |
| 6,498,229 B1 * | 12/2002 | Shalaby | 528/302 |
| 6,503,538 B1 | 1/2003 | Chu et al. | 424/497 |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,524,347 B1 | 2/2003 | Myers et al. | |
| 6,527,801 B1 | 3/2003 | Dutta | 623/1.46 |
| 6,527,863 B1 | 3/2003 | Pacetti et al. | 118/500 |
| 6,528,526 B1 | 3/2003 | Myers et al. | 214/311 |
| 6,530,950 B1 | 3/2003 | Alvarado et al. | 623/1.13 |
| 6,530,951 B1 | 3/2003 | Bates et al. | 623/1.45 |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,755 B2 | 7/2003 | Jackson et al. | 623/1.15 |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 6,616,765 B1 | 9/2003 | Hossainy et al. | 623/1.45 |
| 6,623,448 B2 | 9/2003 | Slater | 604/95.01 |
| 6,625,486 B2 | 9/2003 | Lundkvist et al. | 604/21 |
| 6,645,135 B1 | 11/2003 | Bhat | 600/3 |
| 6,645,195 B1 | 11/2003 | Bhat et al. | 604/528 |
| 6,656,216 B1 | 12/2003 | Hossainy et al. | 623/1.13 |
| 6,656,506 B1 | 12/2003 | Wu et al. | 424/489 |
| 6,660,034 B1 | 12/2003 | Mandrusov et al. | 623/1.42 |

(56) References Cited

U.S. PATENT DOCUMENTS

| | | | |
|---|---|---|---|
| 6,663,662 B2 | 12/2003 | Pacetti et al. | 623/1.13 |
| 6,663,880 B1 | 12/2003 | Roorda et al. | 424/423 |
| 6,666,880 B1 | 12/2003 | Chiu et al. | 623/1.11 |
| 6,673,154 B1 | 1/2004 | Pacetti et al. | 118/500 |
| 6,673,385 B1 | 1/2004 | Ding et al. | 427/2.28 |
| 6,689,099 B2 | 2/2004 | Mirzaee | 604/107 |
| 6,695,920 B1 | 2/2004 | Pacetti et al. | 118/500 |
| 6,706,013 B1 | 3/2004 | Bhat et al. | 604/96.01 |
| 6,709,514 B1 | 3/2004 | Hossainy | 118/52 |
| 6,712,845 B2 | 3/2004 | Hossainy | 623/1.42 |
| 6,713,119 B2 | 3/2004 | Hossainy et al. | 427/2.25 |
| 6,716,444 B1 | 4/2004 | Castro et al. | 424/422 |
| 6,723,120 B2 | 4/2004 | Yan | 623/1.15 |
| 6,733,768 B2 | 5/2004 | Hossainy et al. | 424/426 |
| 6,740,040 B1 | 5/2004 | Mandrusov et al. | 600/439 |
| 6,743,462 B1 | 6/2004 | Pacetti | 427/2.24 |
| 6,749,626 B1 | 6/2004 | Bhat et al. | 623/1.1 |
| 6,753,071 B1 | 6/2004 | Pacetti et al. | 428/212 |
| 6,758,859 B1 | 7/2004 | Dang et al. | 623/1.15 |
| 6,759,054 B2 | 7/2004 | Chen et al. | 424/423 |
| 6,764,505 B1 | 7/2004 | Hossainy et al. | 623/1.15 |
| 7,241,455 B2 | 7/2007 | Richard | 424/423 |
| 8,357,391 B2 * | 1/2013 | Pacetti et al. | 424/426 |
| 2001/0007083 A1 | 7/2001 | Roorda | 623/1.15 |
| 2001/0014717 A1 | 8/2001 | Hossainy et al. | 525/60 |
| 2001/0018469 A1 | 8/2001 | Chen et al. | 523/121 |
| 2001/0020011 A1 | 9/2001 | Mathiowitz et al. | 514/44 |
| 2001/0027340 A1 * | 10/2001 | Wright et al. | 623/1.15 |
| 2001/0029351 A1 | 10/2001 | Falotico et al. | 604/103.02 |
| 2001/0037145 A1 | 11/2001 | Guruwaiya et al. | 623/1.15 |
| 2001/0051608 A1 | 12/2001 | Mathiowitz et al. | 514/44 |
| 2002/0005206 A1 | 1/2002 | Falotico et al. | 128/898 |
| 2002/0007213 A1 | 1/2002 | Falotico et al. | 623/1.21 |
| 2002/0007214 A1 | 1/2002 | Falotico | 623/1.21 |
| 2002/0007215 A1 | 1/2002 | Falotico et al. | 623/1.21 |
| 2002/0009604 A1 | 1/2002 | Zamora et al. | 428/450 |
| 2002/0016625 A1 | 2/2002 | Falotico et al. | 623/1.13 |
| 2002/0032414 A1 | 3/2002 | Ragheb et al. | 604/265 |
| 2002/0032434 A1 | 3/2002 | Chudzik et al. | 604/890.1 |
| 2002/0051730 A1 | 5/2002 | Bodnar et al. | 422/33 |
| 2002/0071822 A1 | 6/2002 | Uhrich | 424/78.27 |
| 2002/0077693 A1 | 6/2002 | Barclay et al. | 623/1.13 |
| 2002/0082679 A1 | 6/2002 | Sirhan et al. | 623/1.15 |
| 2002/0087123 A1 | 7/2002 | Hossainy et al. | 604/198 |
| 2002/0091433 A1 | 7/2002 | Ding et al. | 623/1.2 |
| 2002/0094440 A1 | 7/2002 | Llanos et al. | 428/421 |
| 2002/0111590 A1 | 8/2002 | Davila et al. | 604/265 |
| 2002/0120326 A1 | 8/2002 | Michal | 623/1.15 |
| 2002/0123801 A1 | 9/2002 | Pacetti et al. | 623/1.46 |
| 2002/0142039 A1 | 10/2002 | Claude | 424/486 |
| 2002/0155212 A1 | 10/2002 | Hossainy | 427/2.25 |
| 2002/0165608 A1 | 11/2002 | Llanos et al. | 623/1.45 |
| 2002/0176849 A1 | 11/2002 | Slepian | 424/93.7 |
| 2002/0183581 A1 | 12/2002 | Yoe et al. | 600/3 |
| 2002/0188037 A1 | 12/2002 | Chudzik et al. | 523/112 |
| 2002/0188277 A1 | 12/2002 | Roorda et al. | 604/523 |
| 2003/0004141 A1 | 1/2003 | Brown | 514/152 |
| 2003/0028243 A1 | 2/2003 | Bates et al. | 623/1.15 |
| 2003/0028244 A1 | 2/2003 | Bates et al. | 623/1.15 |
| 2003/0031780 A1 | 2/2003 | Chudzik et al. | 427/2.1 |
| 2003/0032767 A1 | 2/2003 | Tada et al. | 528/310 |
| 2003/0036794 A1 | 2/2003 | Ragheb et al. | 623/1.15 |
| 2003/0039689 A1 | 2/2003 | Chen et al. | 424/468 |
| 2003/0040712 A1 | 2/2003 | Ray et al. | 604/173 |
| 2003/0040790 A1 | 2/2003 | Furst | 623/1.11 |
| 2003/0056920 A1 | 3/2003 | Winheim | 162/207 |
| 2003/0059520 A1 | 3/2003 | Chen et al. | 427/2.1 |
| 2003/0060877 A1 | 3/2003 | Falotico et al. | 623/1.42 |
| 2003/0065377 A1 | 4/2003 | Davila et al. | 623/1.13 |
| 2003/0072868 A1 | 4/2003 | Harish et al. | 427/2.24 |
| 2003/0073961 A1 | 4/2003 | Happ | 604/274 |
| 2003/0083646 A1 | 5/2003 | Sirhan et al. | 604/891.1 |
| 2003/0083739 A1 | 5/2003 | Cafferata | 623/1.42 |
| 2003/0097088 A1 | 5/2003 | Pacetti | 604/19 |
| 2003/0097173 A1 | 5/2003 | Dutta | 623/1.38 |
| 2003/0099712 A1 | 5/2003 | Jayaraman | 424/486 |
| 2003/0105518 A1 | 6/2003 | Dutta | 623/1.38 |
| 2003/0113439 A1 | 6/2003 | Pacetti et al. | 427/2.24 |
| 2003/0139567 A1 | 7/2003 | Kim et al. | 528/354 |
| 2003/0150380 A1 | 8/2003 | Yoe | 118/423 |
| 2003/0157241 A1 | 8/2003 | Hossainy et al. | 427/2.24 |
| 2003/0158517 A1 | 8/2003 | Kokish | 604/103.01 |
| 2003/0190406 A1 | 10/2003 | Hossainy et al. | 427/2.25 |
| 2003/0207020 A1 | 11/2003 | Villareal | 427/2.24 |
| 2003/0211230 A1 | 11/2003 | Pacetti et al. | 427/2.24 |
| 2004/0018296 A1 | 1/2004 | Castro et al. | 427/2.25 |
| 2004/0029952 A1 | 2/2004 | Chen et al. | 514/449 |
| 2004/0047978 A1 | 3/2004 | Hossainy et al. | 427/2.1 |
| 2004/0047980 A1 | 3/2004 | Pacetti et al. | 427/2.25 |
| 2004/0052858 A1 | 3/2004 | Wu et al. | 424/490 |
| 2004/0052859 A1 | 3/2004 | Wu et al. | 424/490 |
| 2004/0054104 A1 | 3/2004 | Pacetti | 526/242 |
| 2004/0060508 A1 | 4/2004 | Pacetti et al. | 118/264 |
| 2004/0062853 A1 | 4/2004 | Pacetti et al. | 427/2.1 |
| 2004/0063805 A1 | 4/2004 | Pacetti et al. | 523/113 |
| 2004/0071861 A1 | 4/2004 | Mandrusov et al. | 427/2.24 |
| 2004/0072922 A1 | 4/2004 | Hossainy et al. | 523/113 |
| 2004/0073298 A1 | 4/2004 | Hossainy | 623/1.46 |
| 2004/0086542 A1 | 5/2004 | Hossainy et al. | 424/423 |
| 2004/0086550 A1 | 5/2004 | Roorda et al. | 424/448 |
| 2004/0096504 A1 | 5/2004 | Michal | 424/471 |
| 2004/0098117 A1 | 5/2004 | Hossainy et al. | 623/1.42 |
| 2004/0215313 A1 | 10/2004 | Chang | 623/1.11 |

FOREIGN PATENT DOCUMENTS

| | | |
|---|---|---|
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| EP | 1 555 278 | 7/2005 |
| EP | 0 684 961 | 12/2006 |
| FR | 2 838 964 | 10/2003 |
| JP | 06-041310 | 2/1994 |
| JP | 07-309938 | 11/1995 |
| JP | 2001-190687 | 7/2001 |
| JP | 2001-517603 | 10/2001 |
| JP | 2004-107670 | 4/2004 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 98/48028 | 10/1998 |
| WO | WO 99/01118 | 1/1999 |

(56) References Cited

FOREIGN PATENT DOCUMENTS

| | | |
|---|---|---|
| WO | WO 99/07343 | 2/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/007588 | 1/2004 |
| WO | WO 2004/009145 | 1/2004 |
| WO | WO 2004/009664 | 1/2004 |

OTHER PUBLICATIONS

Anonymous, *Stenting continues to dominate cardiology*, Clinica 720:22 (Sep. 2, 1996), printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Barrera et al., "Copolymerization and Degradation of Poly(Lactic Acid-Co-Lysine)", Macromolecules, vol. 28, No. 2, Jan. 16, 1995, pp. 425-432.

Chen et al., "Synthesis and Properties of Poly(L-Lactide)-Poly(Ethylene Glycol) Multiblock Copolymers by Coupling Triblock Copolymers", Polymers for Advanced Technologies, vol. 14, No. 3-5, 2003, pp. 245-253.

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Drachman et al., "Neointimal thickening after stent delivery of paclitaxel: change in composition and arrest of growth over six months", Journal of the American College of Cardiology (2000) 36:2325-2332.

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Farnia et al., "Synthesis and Characterization of Novel Biodegradable Triblock Copolymers from L-Lactide, Glycolide, and PPG", Journal of Applied Polymer Science (1999) 73:633-637.

Ferruti et al., "Synthesis and properties of novel block copolymers containing poly(lactic-glycolic acid) and poly(ethyleneglycol) segments", Biomaterials, vol. 16, No. 18, Dec. 1995, pp. 1423-1428.

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Huh et al., "Synthesis and characterization of poly(ethylene glycol)/poly(1-lactic acid) alternating multiblock copolymers", Polymer, vol. 40, No. 22, Oct. 1999, pp. 6147-6155.

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

Kricheldorf et al., "Macrocycles, 8 Multiblock Copoly(Ether-Esters) of Poly(THF) and E-Caprolactone via Macrocyclic Polymerization", Macromol. Chem. and Physics, vol. 200, No. 5, May 1999, pp. 1183-1190.

Kurcok et al., "Anionic Polymerization of Lactones. 14. Anionic Block Copolymerization of σ-Valerolactone and L-Lactide Initiated with Potassium Methoxide", Macromolecules (1992) 25:2285-2289.

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Schmidmaier et al., "Biodegradable poly($_{D,L}$-lactide) Coating of Implants for Continuous Release of Growth Factors", Journal of Biomedical Materials Research—Applied Biomaterials (2001) 58:449-455.

Shigeno, *Prevention of Cerebrovascular Spasm by Bosentan, Novel Endothelin Receptor*; Chemical Abstract 125:212307 (1996).

Södergård et al., "Properties of lactic acid based polymers and their correlalation with composition", Progress in Polymer Science (2002) 27:1123-1163.

(56) References Cited

OTHER PUBLICATIONS van Beusekom et al., *Coronary stent coatings*, Coronary Artery Disease 5(7):590-596 (Jul. 1994).
Wan et al., "Biodegradable poly($_L$-lactide)-poly(ethylene glycol) multiblock copolymer; synthesis and evaluation of cell affinity", Biomaterials (2003) 24:2195-2203.
Wilensky et al., *Methods and Devices for Local Drug Delivery in Coronary and Peripheral Arteries*, Trends Cardiovasc. Med. 3(5):163-170 (1993).
Yokoyama et al., *Characterization of physical entrapment and chemical conjugation of adriamycin in polymeric micelles and their design for in vivo delivery to a solid tumor*, Journal of Controlled Release 50:79-92 (1998).

International Search Report, Written Opinion, and Preliminary Report on Patentability for PCT/US2005/024314 (published Jan. 30, 2007) 22 pages.
Heller et al., "Poly (ortho esters): synthesis, characterization, properties and uses", Advanced Drug Delivery Reviews, 54(7), pp. 1015-1039 (Oct. 16, 2002).
Heller et al., "Poly(ortho esters)", Encyclopedia of Controlled Drug Delivery, vol. 2, Ed. E. Mathiowitz, John Wiley & Sons New York, pp. 852-874 (Jul. 1, 1999).
Lee et al., "Crystallization behavior of poly(l-lactide)-poly(ethylene glycol) multiblock copolymers", European Polymer Journal, 35(12), pp. 2147-2153 (Oct. 11, 1999).

* cited by examiner

COATINGS FOR IMPLANTABLE DEVICES COMPRISING POLY(HYDROXY-ALKANOATES) AND DIACID LINKAGES

CROSS-REFERENCE TO RELATED APPLICATION

This application is a divisional of application Ser. No. 10/902,982, filed Jul. 30, 2004, which is incorporated herein by reference.

FIELD

This invention is directed to coatings for drug delivery devices, such as drug eluting vascular stents, and methods for producing the same.

DESCRIPTION OF THE STATE OF THE ART

Percutaneous transluminal coronary angioplasty (PTCA) is a procedure for treating heart disease, which often manifests itself as stenoses in coronary arteries due to atherosclerosis. A surgeon inserts a catheter assembly having a balloon portion through the skin into a patient's cardiovascular system by way of the brachial or femoral artery. The surgeon positions the catheter assembly across the occlusive lesion. The surgeon inflates the balloon, once positioned, to a predetermined size to radially compress the atherosclerotic plaque of the lesion and to remodel the artery wall. After deflating the balloon, the surgeon withdraws the catheter from the patient's vasculature.

But sometimes this procedure forms intimal flaps or tears arterial linings. These injuries can collapse or occlude the vessel. Moreover, the artery may develop thrombosis and restenosis up to several months after the procedure and may require further angioplasty or a surgical by-pass operation. Implanting a stent into the artery can rectify the injuries and help preserve vascular patency.

In a related manner, local administration of therapeutic agents with stents or stent coatings has reduced restenosis. But even with the progress in stent technology in recent years, stents still can cause undesirable effects. For example, the continued exposure of a stent to blood can lead to thrombus formation itself, and the presence of a stent in a blood vessel can weaken the blood vessel wall over time, which may allow arterial rupture or the formation of an aneurism. A stent can also become so tissue overgrown that it becomes less useful and that its continued presence may cause a variety of problems or complications. Therefore, biodegradable or bioabsorbable stents are desirable to diminish risks that would otherwise associate with the continued presence of a no-longer-needed device at the treatment site.

Polymeric stent coatings can cause adverse and inflammatory reactions in vivo. And there is much less history of using polymerically coated stents, while bare metal stents have an extensive history. Use of absorbable or resorbable coatings also allows for drug release profiles that are difficult to achieve with non-absorbable polymers. Hence, there is great interest in using erodable, absorbable, or resorbable coatings on stents. Next, device coatings with non-fouling properties are desirable. Non-fouling compounds such as poly(ethylene glycol) (PEG) provide these properties. But in order for a copolymer containing PEG to possess non-fouling properties, it is believed that the copolymer must present a high concentration of PEG at the polymer-water interface—to repel protein because repelling proteins requires this. High PEG concentration in the copolymer can deleteriously affect other coating performance aspects. For example, high PEG levels can significantly increase water swelling. This, in turn, can lead to too rapid drug release. It can also reduce the coating's mechanical properties, compromising its durability. Accordingly, there is a need for non-fouling coatings based on biologically absorbable or biologically degradable polymers that are simultaneously non-fouling and that have the drug release and mechanical properties suitable for a coating.

SUMMARY

Embodiments of the current invention relate to block copolymers comprising a poly(hydroxyacid) or poly(hydroxy-alkanoate) block, a block comprising a biocompatible polymer, and a linking moiety.

In some embodiments, the poly(hydroxyacid) or poly(hydroxy-alkanoate) are chosen from specific compounds that are described below. Some embodiments select the biologically compatible polymer to be poly(ethylene glycol) or other polymers that are described below.

Some embodiments select the linking moiety from dicarboxylic acids, diacid chlorides, anhydrides, or from a diisocyanate. In some cases the dicarboxylic acid is selected from specific compounds that are discussed below.

Invention block polymers can have the following formula

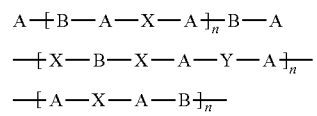

wherein A are poly(hydroxyacid) or poly(hydroxy-alkanoate) blocks, B are blocks of polymeric biocompatible moiety, X is a linking moiety, and n is an integer between about 2 and about 700.

In addition to polymer embodiments, embodiments of the current invention are directed towards methods of making the polymers, coatings made from the polymers, and medical devices comprising those coatings.

DETAILED DESCRIPTION

The following definitions apply:

"Biologically degradable," "biologically erodable," "bioabsorbable," and "bioresorbable" coatings or polymers mean those coatings or polymers that can completely degrade or erode when exposed to bodily fluids such as blood and that the body gradually resorbs, absorbs, or eliminates. The processes of breaking down, absorbing and eliminating the coating or polymer occurs by hydrolysis, metabolic processes, enzymatic processes, bulk or surface degradation, etc.

For purposes of this disclosure "biologically degradable," "biologically erodable," "bioabsorbable," and "bioresorbable" are used interchangeably.

"Biologically degradable," "biologically erodable," "bioabsorbable," or "bioresorbable" stent coatings or polymers mean those coating that, after the degradation, erosion, absorption, or resorption process finishes, no coating remains on the stent. "Degradable," "biodegradable," or "biologically degradable" broadly include biologically degradable, biologically erodable, bioabsorbable, or bioresorbable coatings or polymers.

"Biodegradability," "bioerodability," "bioabsorbability," and "bioresorbability" are those properties of the coating or polymer that make the coating or polymer biologically degradable, biologically erodable, or biologically absorbable, or biologically resorbable.

"Bulk degradation" and "bulk-degrading" refer to degradation processes with several hallmarks. First, the water penetration rate into the polymeric body of the stent or coating is much faster than the polymer hydrolysis or mass loss rate. Next, hydrolysis-induced reduction of the polymer molecular weight occurs throughout the polymeric stent body or stent coating. Certain spatial variations in hydrolysis rate due to a buildup of acidic degradation products within the polymeric body can occur and are termed the autocatalytic effect. The acidic degradation products themselves catalyze further polymer hydrolysis. The mass-loss phase typically occurs later in a bulk degradation process, after the molecular weight of the polymeric body has fallen. As a result, in an idealized bulk-degrading case, the stent or coating mass loss, occurs throughout the entire stent or the coating rather than just at the surface.

The terms "block-copolymer" and "graft copolymer" are defined in accordance with the terminology used by the International Union of Pure and Applied Chemistry (IUPAC). "Block-copolymer" refers to a copolymer containing a linear arrangement of blocks. The block is defined as a portion of a polymer molecule in which the monomeric units have at least one constitutional or configurational feature absent from the adjacent portions. "Graft copolymer" refers to a polymer composed of macromolecules with one or more species of block connected to the main chain as side chains, these side chains having constitutional or configurational features that differ from those in the main chain.

The term "AB block-copolymer" is defined as a block-copolymer having moieties A and B arranged according to the general formula $-\{[A-]_m-[B]_n\}-_x$, where each of "m," "n," and "x" is a positive integer, and m≥2, and n≥2.

The term "ABA block-copolymer" is defined as a block-copolymer having moieties A and B arranged according to the general formula $-\{[A-]_m-[B-]_n-[A]_p\}-_x$, where each of "m," "n," "p," and "x" is a positive integer, and m≥2, and n≥2, and p≥2.

The blocks of the ABA and AB block-copolymers need not be linked on the ends, since the values of the integers determining the number of A and B blocks are such as to ensure that the individual blocks are usually long enough to be considered polymers in their own right. Accordingly, the ABA block copolymer can be named poly A-block-co-poly B block-co-poly A block-copolymer, and the AB block copolymer can be named poly A-block-co-poly B block-copolymer. Blocks "A" and "B," typically, larger than three-block size, can be alternating or random.

The term "poly(hydroxyacid)" refers to polymeric hydroxyacids. Hydroxyacids are substances having at least one hydroxyl group and at least one carboxyl group.

The term "poly(hydroxy-alkanoate)" refers to polymeric hydroxy-alkanoates. Hydroxy-alkanoates are esters of hydroxyacids.

A coating for an implantable medical device, such as a stent, according to embodiments of the present invention, can be a multi-layer structure that can include any of the following four layers or layer combinations:

a primer layer;
a drug-polymer layer (also referred to as "reservoir" or "reservoir layer") or alternatively a polymer-free drug layer;
a topcoat layer; or
a finishing coat layer.

Each coating layer can be formed by dissolving the polymer or polymer blend in a solvent, or a solvent mixture, and applying that solution by spraying it onto the device or immersing the device into the solution. After this application, the coating dries by evaporation. Drying at an elevated temperature accelerates the process. The coating can be annealed between about 40° C. and about 150° C. for between about 5 minutes and about 60 minutes. In some embodiments, annealing the coating improves its thermodynamic stability. Some embodiments require annealing; some embodiments specifically exclude annealing.

To incorporate a drug into the reservoir layer, the drug can be combined with the polymer solution that is applied onto the device, as described above. Alternatively, a polymer-free reservoir can be made. Some embodiments desiring rapid drug release use polymer-free drug reservoirs. To fabricate a polymer free reservoir, the drug can be dissolved in a suitable solvent or mixture of solvents, and the resulting drug solution can be applied on the stent by spraying or immersing the stent in the drug solution.

Alternatively, the drug can be introduced as a colloid system, such as a suspension in an appropriate solvent phase. Depending on a variety of factors, e.g., the nature of the drug, those having ordinary skill in the art can select the suspension solvent the solvent phase of the suspension, as well as the quantity of the drug to be dispersed in it. The suspension can be mixed with a polymer solution and the mixture can be applied on the device as described above. The drug's suspension is applied on the device without being mixed with the polymer solution.

The drug-polymer layer can be applied directly onto at least part of the device surface to store at least one active agent or a drug that is incorporated into the reservoir layer. The optional primer layer can be applied between the device and the reservoir. In some embodiments, this improves the adhesion of the drug-polymer layer to the device. The optional topcoat layer can be applied over at least a portion of the reservoir layer and can serve as a rate limiting membrane, which helps to control the drug release rate. In one embodiment, the topcoat layer can be essentially free from active agents or drugs. If a topcoat layer is used, the optional finishing coat layer can be applied over at least a portion of the topcoat layer for further control of the drug release rate and for improving coating biocompatibility. Without a topcoat layer, the finishing coat layer can be deposited directly on the reservoir layer.

Release of a drug from a coating having both topcoat and finishing coat layers includes at least three steps. First, the polymer of the topcoat layer absorbs a drug at the drug-polymer-topcoat-layer interface. Next, the drug diffuses through the free volume between the topcoat layer macromolecules. Next, the drug arrives at the topcoat-finishing layer interface. Finally, the drug similarly diffuses through the finishing coat layer, arrives at the finish coat layer's outer surface, and these desorb from it into the surrounding tissue or bloodstream. Consequently, topcoat and finishing coat layer combinations, if used, can serve as a rate limiting barrier. The drug can be released through the degradation, dissolution, or erosion of the layer.

In one embodiment, any or all of the layers of the device coating, can be made of a biologically degradable, erodable, absorbable, or resorbable polymer. In another embodiment, the outermost layer of the coating can be limited to such a polymer.

To illustrate in more detail, in a coating having all four layers described above (i.e., the primer, the reservoir layer, the topcoat layer and the finishing coat layer), the outermost layer is the finishing coat layer, which is made of a polymer that is biologically degradable, erodable, absorbable, or resorbable. In this case, the remaining layers (i.e., the primer, the reservoir layer, the topcoat layer) can also comprise a biologically degradable polymer, which can be the same or different in each layer.

If a finishing coat layer is not used, the topcoat layer can be the outermost layer and can be made of a biologically degradable polymer. In these or other embodiments, the remaining layers (i.e., the primer and the reservoir layer) can also comprise a biologically degradable polymer, which can be the same or different in each of the three layers.

If neither a finishing coat layer nor a topcoat layer is used, the device coating may have only two layers, the primer, and the reservoir. The reservoir in this case is the outermost layer of the device coating and can comprise biologically degradable polymer. Optionally, the primer can also comprise a biologically degradable polymer. The two layers can comprise the same or different materials.

The biological degradation, erosion, absorption or resorption of a biologically degradable, erodable, absorbable or resorbable polymer can increase the drug release rate due to the gradual disappearance of the reservoir polymer, the topcoat layer, or both. Whether the release rate increases depends on the drug release rate versus the polymer degradation, erosion, and adsorption or resorption rate. By choosing an appropriate polymer, drug-to-polymer ratio, or concentration, and coating design, the coating can provide either fast or slow drug release, as desired. By choice of the PEG or hydrophilic component content, the hydroxy acid ester bond lability, the polymer molecular weight, in coating design, the polymer can be engineered to show fast or slow degradation. Those having ordinary skill in the art can determine whether a coating having slow or fast release rate is advisable for a particular drug. For example, fast release may be recommended for coatings loaded with antimigratory drugs, which often need to be released within 1 to 2 weeks. For antiproliferative drugs, slow release may be needed (up to 30 days release time).

Biologically degradable, erodable, absorbable, or resorbable polymers that can be used for making any of the stent coating layers include at least one of poly(hydroxyacids), or derivatives thereof, such as poly(hydroxy-alkanoates), or any combination thereof. Examples of poly(hydroxyacids) include any of poly(lactic acids), i.e., poly(D,L-lactic acid) (DLPLA), poly(D-lactic acid), poly(L-lactic acid), poly(L-lactide), poly(D-lactide), poly(D,L-lactide), poly(caprolactone), poly(β-butyrolactone), poly(valerolactone), poly(glycolide), poly(3-hydroxyvaleric acid β-lactone), and poly (dioxanone). Some embodiments specifically exclude any one of or any combination of these poly(hydroxyacids).

Poly(lactic acid), H—[O—CH(CH$_3$)—C(O)]$_n$—OH, can be obtained by ring-opening polymerization of lactide (a cyclic dimer of lactic acid), as demonstrated schematically by Reaction I, where lactide is compound (A) and poly(lactic acid) is compound (B):

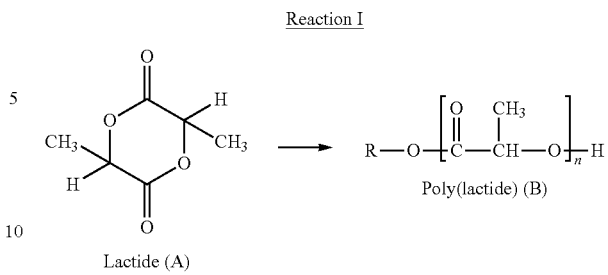

Reaction I

Lactide (A) → Poly(lactide) (B)

The number average molecular weight of poly(lactides) can be between about 5,000 and about 300,000 Daltons, corresponding to the value of the integer n in the compound (B) between about 69 and about 4,166. Those having ordinary skill in the art can determine the conditions under which the transformation of lactide to poly(lactide) illustrated by Reaction I can be carried out.

Polymers including poly(hydroxyacid) or poly(hydroxy-alkanoate) moieties that can be used include block-copolymers illustrated by Formula I:

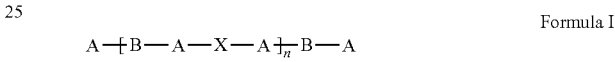

Formula I wherein A are blocks of a poly(hydroxyacids) or a poly (hydroxy-alkanoate), B are blocks of a polymeric biocompatible moiety, X is a linking moiety, and n is an integer having a value between about 1 and about 880, such as, about 2 and about 350, or about 4 and about 175.

A-Blocks

The number average molecular weight of a poly(hydroxy-acid) or poly(hydroxy-alkanoate) A-blocks can be between about 72 and about 100,000 Daltons, more narrowly, between about 360 and about 30,000 Daltons, or about 1000 Daltons.

Instead of poly(lactides), other poly(hydroxyacid) or poly (hydroxy-alkanoate) A-blocks can compose the block-copolymer of Formula I. Examples of some of the poly(hydroxy-alkanoates) that can be used for making the alternative A-blocks include:

poly(3- or 4-hydroxybutyrate) (3-PHB or 4-PHB);
poly(3-hydroxyvalerate) (3-PHV);
poly(3-hydroxybutyrate-co-valerate) (3-PHB-3-HV);
poly(caprolactone) (PCL);
poly(lactide-co-glycolide) (PLGA);
poly(L-lactide);
poly(D-lactide);
poly(D,L-lactide);
poly(L-lactide-co-glycolide);
poly(D,L-lactide-co-glycolide);
poly(L-lactide-co-caprolactone);
poly(D,L-lactide-co-caprolactone);
poly(glycolide-co-caprolactone);
poly(L-lactide-co-D,L-lactide);
poly(L-lactide-co-trimethylene carbonate);
poly(D,L-lactide-co-trimethylene carbonate);
poly(glycolide-co-trimethylene carbonate);
poly(L-lactic acid);
poly(D-lactic acid); or
poly(D,L-lactic acid)

Any mixture of compounds of the groups described above can be also used. In some embodiments, these compounds are selected such that they exclude any one or any combination of the groups described above.

B. B-Blocks

B-blocks are biologically compatible polymers. Examples of suitable biocompatible moieties include:

poly(alkylene glycols), for example, PEG, poly(L-lysine)-graft-co-poly(ethylene glycol), poly(ethylene oxide), poly(propylene glycol) (PPG), poly(tetramethylene glycol), or poly(ethylene oxide-co-propylene oxide);

poly(N-vinyl pyrrolidone);

poly(acrylamide methyl propane sulfonic acid) (AMPS) and salts thereof;

poly(styrene sulfonate);

sulfonated dextran;

polyphosphazenes;

poly(orthoesters);

poly(tyrosine carbonate);

hyaluronic acid and derivatives thereof, for example, hyaluronic acid having a stearoyl or palmitoyl substituent group, copolymers of PEG with hyaluronic acid or with hyaluronic acid-stearoyl, or with hyaluronic acid-palmitoyl;

heparin and derivatives thereof, for example, copolymers of PEG with heparin; or copolymers thereof;

poly(2-hydroxyethyl methacrylate);

a graft copolymer of poly(L-lysine) and poly(ethylene glycol) and mixtures thereof;

poly(2-hydroxyethyl methacrylate);

poly(3-hydroxypropyl methacrylate); or poly(3-hydroxypropyl methacrylamide).

Any mixture of the compounds of these groups can be also used. Some embodiments select these compounds such that any one or any combination of these groups or compounds is specifically excluded.

In some embodiments, the molecular weight of a suitable biocompatible polymeric moiety is chosen such that the patient's kidneys can clear the material from the patient's bloodstream. A molecular weight of a suitable biocompatible polymeric moiety can be below 40,000 Daltons to ensure the renal clearance of the compound, or between about 100 and about 40,000 Daltons, between about 300 and about 20,000 Daltons, or about 1000 Daltons.

C. Linking Moiety X

The linking moiety X in block-copolymer (II) serves to connect two adjacent interior poly(hydroxyacid) or poly(hydroxy-alkanoate) blocks. Moiety X can be derived from a dicarboxylic acid, $(HOOC—(CH_2)_y—COOH)$, from its anhydride, from an acid chloride, from a diisocyanate, such as hexamethylene diisocyanate, 1,4-diisocyanatocyclohexane, or lysine diisocyanate, in which the carboxyl has been converted to an ester or other non-reactive group. One example of a dicarboxylic acid that can be used is succinic acid. Examples of some other dicarboxylic acids that can be used are summarized in Table 1.

TABLE I

Dicarboxylic Acid $(HOOC—(CH_2)_y—COOH)$

| y | Formula | Name |
|---|---|---|
| 0 | HOOC—COOH | oxalic (ethanedioic) acid |
| 1 | HOOC—CH$_2$—COOH | malonic (propanedioic) |
| 3 | HOOC—(CH$_2$)$_3$—COOH | glutaric (pentanedioic) acid |
| 4 | HOOC—(CH$_2$)$_4$—COOH | adipic (hexanedioic) acid |
| 5 | HOOC—(CH$_2$)$_5$—COOH | pimelic (heptanedioic) acid |
| 6 | HOOC—(CH$_2$)$_6$—COOH | suberic (octanedioic) acid |
| 7 | HOOC—(CH$_2$)$_7$—COOH | azelaic (nonanedioic acid) |
| 8 | HOOC—(CH$_2$)$_8$—COOH | sebacic (decanedioic) acid |
| 9 | HOOC—(CH$_2$)$_9$—COOH | nonane-1,9-dicarboxylic (undecanedioic) acid |

TABLE I-continued

Dicarboxylic Acid $(HOOC—(CH_2)_y—COOH)$

| y | Formula | Name |
|---|---|---|
| 10 | HOOC—(CH$_2$)$_{10}$—COOH | decane-1,10-dicarboxylic (dodecanedioic) acid |
| 11 | HOOC—(CH$_2$)$_{11}$—COOH | brassylic (tridecanedioic) acid |
| 12 | HOOC—(CH$_2$)$_{12}$—COOH | dodecane-1,12-dicarboxylic (tetradecanedioic) acid |
| 13 | HOOC—(CH$_2$)$_{13}$—COOH | tridecane-1,13-dicarboxylic (pentadecanedioic) acid |
| 14 | HOOC—(CH$_2$)$_{14}$—COOH | thapsic (hexadecanedioic) acid |
| NA | HOOC—(C$_6$H$_4$)—COOH | terephthalic acid |
| NA | HOOC—(C$_2$H$_2$)—COOH | fumaric acid |
| NA | HOOC—(C$_2$H$_2$)—COOH | maleic acid |
| NA | HOOC—(CH$_2$COCH$_2$)—COOH | 1,3-acetonedicarboxylic acid |

Any mixture of dicarboxylic acids shown in Table I, or their anhydrides, can be also used. In some embodiments, the dicarboxylic acid is specifically selected to exclude any one or any combination of the acids listed in Table I.

Block-copolymer shown by Formula I can be synthesized by standard methods known to those having ordinary skill in the art, for example, polycondensation of PEG with PLA, followed by reaction with a dicarboxylic acid or anhydride, or acid chloride, or chloroanhydride.

One way of synthesizing a Formula I block-copolymer is a two-step process, comprising, first, ring opening polymerization and, second, a coupling step. Ring opening polymerization comprises reacting lactide with PEG, where PEG is used as a macroinitiator. Condensation can occur at an elevated reaction temperature (about 140° C.), neat or in a solvent, such as toluene, in the presence of stannous octanoate. to this yields a hydroxyl-terminated, triblock-copolymer PLA-PEG-PLA. Coupling comprises further reacting the PLA-PEG-PLA triblock-copolymer with a dicarboxylic acid or anhydride to connect the chains. For example, succinic or adipic, acid or anhydride can be used as the dicarboxylic acid. Coupling can be carried out in the presence of a coupling agent, such as 1,3-dicyclohexylcarbodiimide (DCC). Instead of DCC, 1-ethyl-3-(3-dimethylaminopropyl)carbodiimide (EDC) can be used. With carbodiimides, a catalyst such as N-dimethylaminopyridine (DMAP), diazabicycloundecane (DBU), N-(methylpolystyrene)-4-(methylamino)pyridine, or 4-pyrrolidinopyridine is used in coupling. Instead of the dicarboxylic acid or anhydride, a diisocyanate or diacid chloride can be used.

In some embodiments, using succinic anhydride as an anhydride, the obtained block copolymer, as in Formula I, can obtained, in which poly(D,L-lactide) serves as A-blocks, poly(ethylene-glycol) as B-blocks, and the succinic-acid-derived group, —CO—(CH$_2$)$_1$2-COOH—, serves as the linking moiety X. One possible structure of such a block-copolymer is shown by Formula II:

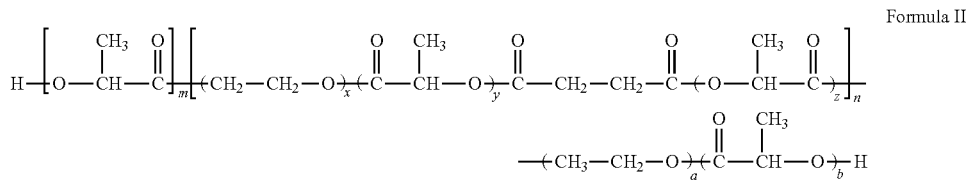

Formula II

The block-copolymer shown by Formula II can have a total number-average molecular weight between about 2000 and about 200,000 Daltons, or about 45,000 Daltons. The value of the integer m can be between about 2 and about 700, or about 10. The value of the integer n can be between about 2 and about 700, or about 10. The value of the integer x can be between about 5 and about 100, or about 14. The value of the integer y can be between about 2 and about 700, or about 10. The value of the integer z can be between about 2 and about 700, or about 10. The value of the integer a can be between about 5 and about 100, or about 14. The value of the integer b can be between about 2 and about 700, or about 10.

In these or other embodiments, instead of dicarboxylic acid or anhydride, a chloroanhydride of a dicarboxylic acid can be used in chain extending. For example, adipoyl, sebacyl, or terephthaloyl chloride can be used. In this reaction, HCl, which is released as a by-product, can be neutralized to avoid hydrolyzing the PLA blocks. Common neutralizing agents are triethylamine and pyridine. Those having ordinary skill in the art can determine how to neutralize HCl. In some embodiments, a bromoanhydride of a dicarboxylic acid can be used in chain extending.

According to another embodiment of the present invention, the step sequence can be reversed. Condensation can comprise reacting an alpha-hydroxy acid, such as lactic acid, with a dicarboxylic acid or anhydride, to obtain a poly(lactic acid)-dicarboxylic acid adduct with carboxyl end groups. Coupling comprises further reacting the PLA-dicarboxylic acid adduct with a hydroxy-terminated, biocompatible molecules such as PEG. Coupling can be carried out in the presence of a coupling agent, such as DCC or, alternatively, EDC, and a catalyst such as DMAP. This scheme gives rise to a very similar multi-block copolymer with the formula:

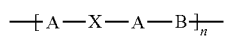

where the A and B blocks are defined as before.

According to yet another embodiment of the invention, a block copolymer is made wherein the poly(hydroxy acid) and polymeric, biocompatible moieties are reacted separately, and then coupled. Specifically, a first block is made by reacting a hydroxy-terminated polymeric, biocompatible moiety, such as PEG with a diacid or anhydride as shown below in Reaction II.

Reaction II

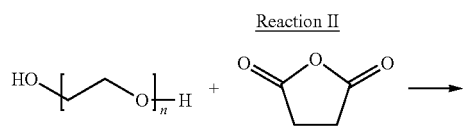

-continued

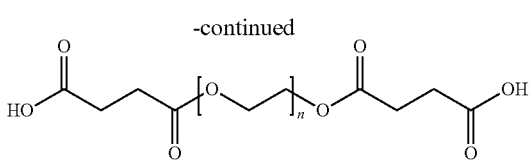

A second block is made by ring opening polymerization with a cyclic hydroxy-alkanoate, such as lactide, using a dihydric initiator, such as 1,3-propanediol, as shown in Reaction III.

Reaction III

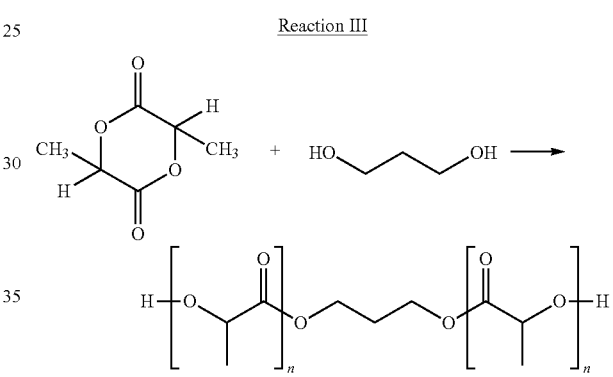

These two blocks are then coupled together using a coupling agent, such as DCC or EDC, facilitated by a catalyst such as N-dimethylaminopyridine (DMAP), diazabicycloundecane (DBU), N-(methylpolystyrene)-4-(methylamino)pyridine, or 4-pyrrolidinopyridine. This embodiment may be described by Formula III, below:

Formula III

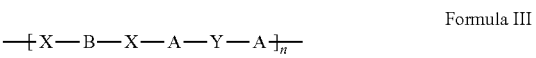

wherein, A-blocks and B-blocks, and linking moiety X are as described before. Linking moiety Y is a dihydric moiety that can be ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,4-cyclohexanedimethanol, 1,4-hydroxymethylbenzene, serinol, dihydroxyacetone, any linear or branched $C_2$ to $C_{12}$ hydrocarbon with two primary hydroxyl groups, and any linear or branched $C_2$ to $C_{12}$ with unsaturation and two primary hydroxyl groups. In some embodiments, the Y-moiety is selected to specifically exclude any one or any combination of those listed above.

Any layer of the coating can contain any amount of the bioabsorbable polymer(s) described above, or a blend of more than one such polymer. If less than 100% of the layer comprises a bioabsorbable polymer(s) described above, other, alternative, polymers can comprise the balance. Examples of the alternative polymers that can be used include poly-acrylates, such as poly(butyl methacrylate), poly(ethyl methacrylate), poly(ethyl methacrylate-co-butyl methacrylate), poly(acrylonitrile), poly(ethylene-co-methyl methacrylate), poly(acrylonitrile-co-styrene), and poly(cyanoacrylates); fluorinated polymers or copolymers, such as poly(vinylidene fluoride) and poly(vinylidene fluoride-co-hexafluoro propene); poly(N-vinyl pyrrolidone); polydioxanone; polyorthoester; polyanhydride; poly(L-lactide); poly(D,L-lactide); poly(D-lactide); poly(glycolide); poly(lactide-co-glycolide); poly(caprolactone); poly(3-hydroxybutyrate); poly(4-hydroxybutyrate); poly(3-hydroxybutyrate-co-3-hydroxyvalerate); poly(glycolic acid); poly(glycolic acid-co-trimethylene carbonate); polyphosphoester; polyphosphoester urethane; poly(amino acids); poly(trimethylene carbonate); poly(iminocarbonate); co-poly(ether-esters); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; vinyl halide polymers and copolymers, such as polyvinyl chloride; polyvinyl ethers, such as polyvinyl methyl ether; polyvinylidene chloride; polyvinyl ketones; polyvinyl aromatics such as polystyrene; polyvinyl esters such as polyvinyl acetate; copolymers of vinyl monomers with each other and olefins, e.g., poly(ethylene-co-vinyl alcohol) (EVAL); ABS resins; and poly(ethylene-co-vinyl acetate); polyamides such as Nylon 66 and polycaprolactam; alkyd resins; polycarbonates; polyoxymethylenes; polyimides; polyethers, epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose. Some embodiments select the alternate polymers to specifically exclude any one or any combination of the alternate polymers listed above.

Representative examples of some solvents suitable for making the stent coatings include N,N-dimethylacetamide (DMAC), N,N-dimethylformamide (DMF), tetrahydrofuran (THF), cyclohexanone, xylene, toluene, acetone, i-propanol, methyl ethyl ketone, propylene glycol monomethyl ether, methyl butyl ketone, ethyl acetate, n-butyl acetate, and dioxane. Some solvent mixtures can be used as well. Representative examples of the mixtures include:

DMAC and methanol (e.g., a 50:50 by mass mixture);
water, i-propanol, and DMAC (e.g., a 10:3:87 by mass mixture);
i-propanol, and DMAC (e.g., 80:20, 50:50, or 20:80 by mass mixtures);
acetone and cyclohexanone (e.g., 80:20, 50:50, or 20:80 by mass mixtures);
acetone and xylene (e.g. a 50:50 by mass mixture);
acetone, FLUX REMOVER AMS, and xylene (e.g., a 10:50:40 by mass mixture); and
1,1,2-trichloroethane and chloroform (e.g., an 80:20 by mass mixture).

FLUX REMOVER AMS is trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance of methanol, with trace amounts of nitromethane. Those having ordinary skill in the art will select the solvent or a mixture of solvents suitable for a particular polymer being dissolved.

Some embodiments comprise invention polymers coated onto a medical device containing or constructed from a polymer, a medical device containing or constructed from a metal, or a bare medical device, or invention polymers coated on top of drug coatings already present on a medical device. Alternatively, some embodiments comprise invention polymers disposed between a medical device and a drug coating. Also, some embodiments comprise invention polymers composing polymer-based medical devices or invention polymers composing medical device substrates (implantable or not). Some invention embodiments comprise medical devices not made from polymer-containing or -constructed stents. Some invention embodiments comprise stents not made from metal-containing or constructed stents.

In some embodiments, invention polymers serve as the base material for coatings on medical devices. In some embodiments, coatings may contain a primer layer. Some embodiments exclude a primer layer. In some embodiments, invention polymers serve as a topcoat on drug reservoir layers either that contain or do not contain polymers. Some embodiments employ an additional polymer layer on top of the invention polymer. This top layer can be another layer of inventive polymer, a typical plasma polymerized layer, a layer polymerized without a plasma source, or any combination of these. Of these embodiments, some specifically exclude layers of additional inventive polymers, typical plasma polymerized layers, layers polymerized without a plasma source, or any combination of these.

Some embodiments add conventional drugs, such as small, hydrophobic drugs, to invention polymers (as discussed in any of the embodiments, above), making them biostable, drug systems. Some embodiments graft-on conventional drugs or mix conventional drugs with invention polymers. Invention polymers can serve as base or topcoat layers for biobeneficial polymer layers. In some embodiments, a drug is any substance capable of exerting a therapeutic, diagnostic, or prophylactic effect in a patient.

The selected drugs can inhibit vascular, smooth muscle cell activity. More specifically, the drug activity can aim at inhibiting abnormal or inappropriate migration or proliferation of smooth muscle cells to prevent, inhibit, reduce, or treat restenosis. The drug can also include any substance capable of exerting a therapeutic or prophylactic effect in the practice of the present invention. Examples of such active agents include antiproliferative, antineoplastic, antiinflammatory, antiplatelet, anticoagulant, antifibrin, antithrombin, antimitotic, antibiotic, and antioxidant substances, as well as their combinations, and any prodrugs, metabolites, analogs, congeners, derivatives, salts and their combinations.

An example of an antiproliferative substance is actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin I1, actinomycin X1, and actinomycin C1. Examples of antineoplastics include paclitaxel and docetaxel. Examples of antiplatelets, anticoagulants, antifibrins, and antithrombins include aspirin, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocor). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck & Co., Whitehouse Station, N.J.), calcium channel blockers (such as Nifedipine), colchicine, fibroblast growth factor (FGF) antagonists, histamine antagonist, LOVASTATIN (an inhibitor of HMG-CoA reductase, a cholesterol lowering drug from Merck & Co.), monoclonal antibodies (such as PDGF receptors), nitroprusside, phosphodiesterase inhibitors, prostaglandin inhibitor (available from Glazo), Seramin (a PDGF antagonist), serotonin blockers, thioprotease inhibitors, triazolopyrimidine (a PDGF antagonist), and nitric oxide. Other useful drugs may include alpha-interferon, genetically engineered epithelial cells, dexamethasone, estradiol, clobetasol propionate, cisplatin, insulin sensitizers, receptor tyrosine kinase inhibitors, and carboplatin. Exposure of the composition to the drug should not adversely alter the drug's composition or characteristic. Accordingly, drug containing embodiments choose drugs that are compatible with the composition. Rapamycin is a suitable drug. Additionally, 40-O-(2-hydroxy)ethyl-rapamycin, or a functional analog or structural derivative thereof, is suitable, as well. Examples of analogs or derivatives of 40-O-(2-hydroxy)ethyl-rapamycin include, among others, 40-O-(3-hydroxy)propyl-rapamycin and 40-O-2-(2-hydroxy) ethoxyethyl-rapamycin. Those of ordinary skill in the art know of various methods and coatings for advantageously controlling the release rate of drugs, such as 40-O-(2-hydroxy)ethyl-rapamycin.

Some embodiments choose the drug such that it does not contain at least one of or any combination of antiproliferative, antineoplastic, antiinflammatory, antiplatelet, anticoagulant, antifibrin, antithrombin, antimitotic, antibiotic, or antioxidant substances, or any prodrugs, metabolites, analogs, congeners, derivatives, salts or their combinations.

Some invention embodiments choose the drug such that it does not contain at least one of or any combination of actinomycin D, derivatives and analogs of Actinomycin D, dactinomycin, actinomycin IV, actinomycin I1, actinomycin X1, actinomycin C1, paclitaxel, docetaxel, aspirin, sodium heparin, low molecular weight heparin, hirudin, argatroban, forskolin, vapiprost, prostacyclin, prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor and 7E-3B, methotrexate, azathioprine, vincristine, vinblastine, fluorouracil, adriamycin, mutamycin, angiopeptin, angiotensin converting enzyme inhibitors, CAPTOPRIL, CILAZAPRIL, or LISINOPRIL, calcium channel blockers, Nifedipine, colchicine, fibroblast growth factor (FGF) antagonists, histamine antagonist, LOVASTATIN, monoclonal antibodies, PDGF receptors, nitroprusside, phosphodiesterase inhibitors, prostaglandin inhibitor, Seramin, PDGF antagonists, serotonin blockers, thioprotease inhibitors, triazolopyrimidine, nitric oxide, alpha-interferon, genetically engineered epithelial cells, dexamethasone, estradiol, clobetasol propionate, cisplatin, insulin sensitizers, receptor tyrosine kinase inhibitors, carboplatin, Rapamycin, 40-O-(2-hydroxy)ethyl-rapamycin, or a functional analogs of 40-O-(2-hydroxy)ethyl-rapamycin, structural derivative of 40-O-(2-hydroxy)ethyl-rapamycin, 40-O-(3-hydroxy)propyl-rapamycin, and 40-O-2-(2-hydroxy)ethoxyethyl-rapamycin, or any prodrugs, metabolites, analogs, congeners, derivatives, salts or their combinations.

Some invention embodiments comprise a drug or drug combination, and some require a drug or combination of drugs. Of the drugs specifically listed above, some invention embodiments exclude a single or any combination of these drugs.

Some embodiments comprise invention polymers combined with other polymers in multilayer arrangements. For example, an invention polymer could under- or over-lay another polymer such as a polymer coated on a device, a medical device, an implantable medical device, or a stent. In some embodiments, invention polymers do not underlay another polymer; in other embodiments, invention polymers must overlay another polymer.

Some invention embodiments define the genera of medical devices to exclude at least one of self-expandable stents, balloon-expandable stents, stent-grafts, grafts (e.g., aortic grafts), vascular grafts, artificial heart valves, cerebrospinal fluid shunts, pacemaker electrodes, guidewires, ventricular assist devices, artificial hearts, cardiopulmonary by-pass circuits, blood oxygenators, or endocardial leads.

Some invention embodiments comprise multilayered structures in which an invention polymer is present in one or more of the layers of the multilayered structure.

The drug-polymer layer can be applied directly onto at least a part of the medical device surface to serve as a reservoir for at least one active agent or a drug. An optional primer layer can be applied between the device and the reservoir to improve polymer adhesion to the medical device. Some embodiments apply the topcoat layer over at least a portion of the reservoir layer, and the topcoat layer serves as a rate limiting membrane, which helps to control the rate of release of the drug.

Implantable medical devices are also within the scope of the invention. Examples of such implantable devices include stents, stent-grafts, grafts (e.g., aortic grafts), artificial heart valves, abdominal aortic aneurysm devices, cerebrospinal fluid shunts, pacemaker electrodes, and endocardial leads (e.g., FINELINE and ENDOTAK, available from Guidant Corporation). The underlying structure of the device can be of virtually any design. The device can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

EXAMPLES

The following examples are provided to further illustrate embodiments of the present invention.

Example 1

Synthesis of multi-block PEG300-Poly(D,L-lactide), 30/70 weight ratio, coupled by succinic acid.

To a 250 ml, three necked flask, equipped with magnetic stirring, vacuum, and argon purge is added PEG300 (37.5 gm (0.125 mole). Using an oil bath, the PEG is heated to 105° C., and stirred under vacuum for two hours to remove water. The flask is purged with argon, and D,L-lactide (76.94 g, 0.534 mole) is added, and vacuum applied with stirring for another 30 minutes. After purging with argon, the flask is heated to 140° C., and polymerization is initiated by adding 10.8 ml of a 5% (w/w) stannous-octanoate-dry-toluene solution. After stirring for 24 hours, the reaction solution is cooled and poured into 500 ml of cold methanol to precipitate the polymer. The polymer is washed with methanol/petroleum ether and dried under vacuum. The triblock copolymer from above (25 g, $4.17 \times 10^{-4}$ mole) and succinic anhydride (0.0417 g, $4.17 \times 10^{-4}$ mole) is dissolved in 200 ml of anhydrous dichloromethane. To this is added 1,3-dicyclohexylcarbodiimide (0.103 g, $5 \times 10^{-4}$ mole) and 4-dimethylaminopyridine (0.0012 g, $1 \times 10^{-5}$ mole). After stirring at room temperature for 24 hours, the reaction solution is centrifuged to precipitate dicyclohexylurea and the supernatant solution poured into 150 ml of cold methanol to precipitate the polymer. After filtration, the polymer is washed with methanol/petroleum ether and dried under vacuum.

Example 2

Synthesis of multi-block PEG600-Poly(D,L-lactide), 10/90 weight ratio, coupled by hexamethylene diisocyanate.

To a 250 ml, three necked flask, equipped with magnetic stirring, vacuum, and argon purge is added PEG600 (12.5 gm (0.0208 mole). Using an oil bath, the PEG is heated to 105° C., and stirred under vacuum for two hours to remove water. The flask is purged with argon and D,L-lactide (109.4 g, 0.76 mole) is added, and the vacuum applied with stirring for another 30 minutes. After purging with argon, the flask is heated to 140° C., and polymerization initiated by addition of 15.4 ml of a 5% (w/w) solution of stannous octanoate in dry toluene. After stirring for 24 hours, 1,6-diisocyanatohexane (10.13 g, 0.0602 mole) as a 10% solution in dry dimethylformamide is added and the solution stirred at 140° C. for another hour. The reaction solution is cooled and poured into 500 ml of cold methanol to precipitate the polymer. The polymer is washed with methanol/petroleum ether and dried under vacuum. The triblock copolymer from above (25 g, $4.17 \times 10^{-4}$ mole) and succinic anhydride (0.0417 g, $4.17 \times 10^{-4}$ mole) is dissolved in 200 ml of anhydrous dichloromethane. To this is added 1,3-dicyclohexylcarbodiimide (0.103 g, $5 \times 10^{-4}$ mole) and 4-dimethylaminopyridine (0.0012 g, $1 \times 10^{-5}$ mole). After stirring at room temperature for 24 hours, the reaction solution is centrifuged to precipitate dicyclohexylurea and the supernatant solution poured into 150 ml of cold methanol to precipitate the polymer. After filtration, the polymer is washed with methanol/petroleum ether and dried under vacuum.

Example 3

Use of the polymer from example 1 as a biocompatible topcoat

A first composition can be prepared by mixing the following components:
about 2.0 mass % poly(D,L-lactide); and
the balance, acetone.

The first composition can be applied onto the surface of bare 12 mm small VISION stent (available from Guidant Corporation). The coating can be sprayed and dried to form a primer layer. A spray coater can be used having a 0.014 round nozzle maintained at ambient temperature with a feed pressure 2.5 psi (0.17 atm) and an atomization pressure of about 15 psi (1.02 atm). About 20 μg of the coating can be applied at per one spray pass. Between the spray passes, the stent can be dried for about 10 seconds in a flowing air stream at about 50° C. About 110 μg of wet coating can be applied. The stents can be baked at about 80° C. for about one hour, yielding a primer layer composed of approximately 100 μg of poly(D,L-lactide)

A second composition can be prepared by mixing the following components:
about 2.0 mass % poly(D,L-lactide);
about 1.0 mass % everolimus; and
the balance, a 50/50 blend (w/w) of acetone and 2-butanone.

The second composition can be applied onto the dried primer layer, using the same spraying technique and equipment used for applying the primer layer, to form the drug-polymer layer. About 180 μg of wet coating can be applied followed by drying and baking at about 50° C. for about 1 hour, yielding a dry drug-polymer layer having solids content of about 170 μg.

A third composition can be prepared by mixing the following components:
about 2.0 mass % the polymer of example 1; and
the balance, a 50/50 blend (w/w) of acetone and chloroform.

The third composition can be applied onto the dried drug-polymer layers, using the same spraying technique and equipment used for applying the primer and drug-polymer layers, to form a topcoat layer. About 110 μg of wet coating can be applied followed by drying and baking at about 50° C. for about 1 hour, yielding a dry topcoat layer having solids content of about 100 μg.

Example 4

Use of the polymer from example 1 as a drug/polymer reservoir coating

A first composition can be prepared by mixing the following components:
about 2.0 mass % poly(D,L-lactide); and
the balance, acetone.

The first composition can be applied onto the surface of bare 12 mm small VISION stent (available from Guidant Corporation). The coating can be sprayed and dried to form a primer layer. A spray coater can be used having a 0.014 round nozzle maintained at ambient temperature with a feed pressure 2.5 psi (0.17 atm) and an atomization pressure of about 15 psi (1.02 atm). About 20 μg of the coating can be applied at per one spray pass. Between the spray passes, the stent can be dried for about 10 seconds in a flowing air stream at about 50° C. About 110 μg of wet coating can be applied. The stents can be baked at about 80° C. for about one hour, yielding a primer layer composed of approximately 100 μg of poly(D,L-lactide)

A second composition can be prepared by mixing the following components:
about 2.0 mass % the polymer of example 2;
about 0.5%; paclitaxel
the balance, a 50/50 blend (w/w) of acetone and chloroform.

The second composition can be applied onto the dried primer layer, using the same spraying technique and equipment used for applying the primer layer, to form the drug-polymer layer. About 150 μg of wet coating can be applied followed by drying and baking at about 50° C. for about 1 hour, yielding a dry drug-polymer layer having solids content of about 140 μg.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true spirit and scope of the embodiments of this invention.

Additionally, various embodiments have been described above. For convenience's sake, combinations of aspects (such as monomer or initiator type) composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists in which that aspect specifically excludes that aspect.

Moreover, some embodiments recite ranges. When this is done, it is meant to disclose the ranges as a range, and to disclose each and every point within the range, including end points. For those embodiments that disclose a specific value or condition for an aspect, supplementary embodiments exist that are otherwise identical, but that specifically include the value or the conditions for the aspect.

What is claimed is:

1. A polymer having the formula:

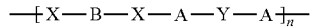

wherein:
A are poly(hydroxyacid) or poly(hydroxy-alkanoate) blocks;
B are blocks of a biologically compatible polymer;
X is a linking moiety;
Y is a dihydric moiety; and
n is an integer between 2 and 700;
wherein the linking moiety is derived from at least one of, or any combination of, oxalic acid, malonic acid, succinic acid, glutaric acid, adipic acid, pimelic acid, brassylic acid, dodecane-1,12-dicarboxylic acid, tridecane-1,13-dicarboxylic acid, thapsic acid, fumaric acid, maleic acid, and 1,3-acetonedicarboxylic acid; and
wherein the biologically compatible polymer is poly(L-lysine)-graft-co-poly(ethylene glycol).

2. The polymer of claim 1, wherein the poly(hydroxyacid) or poly(hydroxy-alkanoate) is one of poly(lactide-co-glycolide); poly(L-lactide); poly(D-lactide); poly(D,L-lactide); poly(L-lactide-co-glycolide); poly(D,L-lactide-co-glycolide); poly(L-lactide-co-caprolactone); poly(D,L-lactide-co-caprolactone); poly(L-lactide-co-D,L-lactide); poly(L-lactide-co-trimethylene carbonate); poly(D,L-lactide-co-trimethylene carbonate); poly(L-lactic acid); poly(D-lactic acid); poly(D,L-lactic acid); or a combination thereof.

3. The polymer of claim 1, wherein Y is ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,4-cyclohexanedimethanol, 1,4-hydroxymethylbenzene, serinol, dihydroxyacetone, any linear or branched $C_2$ to $C_{12}$ hydrocarbon with two primary hydroxyl groups, or any linear or branched $C_2$ to $C_{12}$ with unsaturation and two primary hydroxyl groups.

4. The polymer of claim 1 wherein the poly(hydroxyacid) or poly(hydroxy-alkanoate) is one of poly(L-lactide); poly(D-lactide); poly(D,L-lactide); poly(L-lactide-co-D,L-lactide); poly(L-lactic acid); poly(D-lactic acid); poly(D,L-lactic acid); or a combination thereof.

5. The polymer of claim 1 wherein the linking moiety is derived from at least one of or any combination of malonic acid, succinic acid, glutaric acid, adipic acid, pimelic acid, brassylic acid, dodecane-1,12-dicarboxylic acid, tridecane-1,13-dicarboxylic acid, thapsic acid, fumaric acid, maleic acid, and 1,3-acetonedicarboxylic acid.

6. The polymer of claim 1 wherein the linking moiety is derived from at least one of or any combination of glutaric acid, adipic acid, pimelic acid, brassylic acid, dodecane-1,12-dicarboxylic acid, tridecane-1,13-dicarboxylic acid, thapsic acid, fumaric acid, maleic acid, and 1,3-acetonedicarboxylic acid.

7. The polymer of claim 1 wherein each A is a poly(D,L-lactide) block.

8. The polymer of claim 7 wherein n is about 10.

9. A method of making a polymer comprising:
reacting a hydroxy-terminated polymeric, biocompatible moiety with a diacid or anhydride to make a first block;
making a second block by ring opening polymerization with a cyclic hydroxy-alkanoate using a dihydric initiator;
coupling the first block to the second block using a coupling agent, facilitated by a catalyst, such that a final block copolymer is formed having the formula:

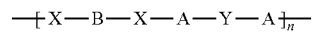

wherein:
A are poly(hydroxyacid) or poly(hydroxy-alkanoate) blocks;
B are blocks of a biologically compatible polymer;
X is a linking moiety;
Y is a dihydric moiety; and
n is an integer between 2 and 700;
wherein the linking moiety is derived from at least one of, or any combination of, oxalic acid, malonic acid, succinic acid, glutaric acid, adipic acid, pimelic acid, brassylic acid, dodecane-1,12-dicarboxylic acid, tridecane-1,13-dicarboxylic acid, thapsic acid, fumaric acid, maleic acid, and 1,3-acetonedicarboxylic acid; and
wherein the biologically compatible polymer is poly(L-lysine)-graft-co-poly(ethylene glycol).

10. The method of claim 9, wherein the hydroxy-terminated polymeric, biocompatible moiety is poly(ethylene glycol) (PEG).

11. The method of claim 9, wherein the cyclic hydroxy-alkanoate is lactide.

12. The method of claim 10, wherein the dihydric initiator is 1,3-propanediol.

13. The method of claim 9, wherein the coupling agent is 1,3-dicyclohexylcarbodiimide (DCC) or 1-ethyl-3-(3-dimethylaminopropyl)carbodiimide (EDC).

14. The method of claim 9, wherein the catalyst is N-dimethylaminopyridine (DMAP), diazabicycloundecane (DBU), N-(methylpolystyrene)-4-(methylamino)pyridine, or 4-pyrrolidinopyridine.

15. The method of claim 9, wherein Y is ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,4-cyclohexanedimethanol, 1,4-hydroxymethylbenzene, serinol, dihydroxyacetone, any linear or branched $C_2$ to $C_{12}$ hydrocarbon with two primary hydroxyl groups, or any linear or branched $C_2$ to $C_{12}$ with unsaturation and two primary hydroxyl groups.

16. The method of claim 9, wherein the poly(hydroxyacid) or poly(hydroxy-alkanoate) is one of poly(lactide-co-glycolide); poly(L-lactide); poly(D-lactide); poly(D,L-lactide); poly(L-lactide-co-glycolide); poly(D,L-lactide-co-glycolide); poly(L-lactide-co-caprolactone); poly(D,L-lactide-co-caprolactone); poly(L-lactide-co-D,L-lactide); poly(L-lactide-co-trimethylene carbonate); poly(D,L-lactide-co-trimethylene carbonate); poly(L-lactic acid); poly(D-lactic acid); poly(D,L-lactic acid); or a combination thereof.

17. The method of claim 9 wherein the linking moiety is derived from at least one of or any combination of malonic acid, succinic acid, glutaric acid, adipic acid, pimelic acid, brassylic acid, dodecane-1,12-dicarboxylic acid, tridecane-1,13-dicarboxylic acid, thapsic acid, fumaric acid, maleic acid, and 1,3-acetonedicarboxylic acid.

18. The method of claim 9 further comprising:
depositing the final block copolymer on a region of an implantable portion of a medical device.

19. The method of claim 18 wherein the medical device is a stent.

20. A coating made with the polymer of claim 1.

21. A medical device comprising the coating of claim 20.

\* \* \* \* \*